(12) United States Patent
Jiang

(10) Patent No.: US 12,076,263 B2
(45) Date of Patent: Sep. 3, 2024

(54) ADJUSTABLE TOE ORTHOTIC DEVICE

(71) Applicant: Hangzhou Moenmedic Health Technology Co., Ltd, Zhejiang (CN)

(72) Inventor: Junfei Jiang, Zhejang (CN)

( * ) Notice: Subject to any disclaimer, the term of this patent is extended or adjusted under 35 U.S.C. 154(b) by 256 days.

(21) Appl. No.: 17/534,469

(22) Filed: Nov. 24, 2021

(65) Prior Publication Data
US 2022/0168127 A1 Jun. 2, 2022

(30) Foreign Application Priority Data
Nov. 30, 2020 (CN) .......................... 202022839922.5

(51) Int. Cl.
*A61F 5/01* (2006.01)
(52) U.S. Cl.
CPC .............. *A61F 5/019* (2013.01); *A61F 5/012* (2013.01)
(58) Field of Classification Search
CPC .. A61F 5/019; A61F 5/012; A61F 5/01; A61F 5/00; A61F 5/0193; A61F 5/0585; A61F 5/058
See application file for complete search history.

(56) References Cited

U.S. PATENT DOCUMENTS

| | | | |
|---|---|---|---|
| 2005/0187506 A1* | 8/2005 | Reinhardt | A61F 5/019 602/30 |
| 2011/0082405 A1* | 4/2011 | Domangue | A61F 5/019 602/30 |

* cited by examiner

*Primary Examiner* — Tarla R Patel

(57) ABSTRACT

A medical auxiliary equipment, in particular to an adjustable toe orthotic device, with a primary support and a secondary support connected by rotation; the primary and secondary supports are both provided with bandages, separately used for tying the primary support to the arch of the foot and the secondary support to the toe. Pivots of the primary and secondary supports are arranged with a lifting component, which is used to abut on the deformity point of the toe, and by adjusting the lifting distance of the lifting component, it adapts to different degrees of toe deformity. The device adapts to different toe deformities through the adjustment of the lifting degree of the abutting surface, so that the orthotic abutment of the toe orthotic device is always in the state that best matches the toe deformity of users.

5 Claims, 4 Drawing Sheets

ADJUSTABLE TOE ORTHOTIC DEVICE

BACKGROUND OF THE INVENTION

1. Field of the Invention

The utility model belongs to the technical field of medical auxiliary equipment, in particular to an adjustable toe orthotic device.

2. Description of Related Art

Nowadays, that people wear shoes improperly or the shoes don't fit well, or other reasons has caused deformity or valgus of toes, etc., hence feet bone orthotic device is required. Chinese Utility Model 201620902457.6 discloses a new type of toe orthotic device, including a primary support, a rotary support and bandages. One end of the primary support is provided with multiple bandage mounting holes for the bandage to pass through, and one end of the rotary support is also provided multiple bandage mounting holes for the bandage to pass through; the primary support is connected with the rotary support by a rotary mechanism; the device further includes a soft inner pad, and the soft inner pad is fixed on the inner end surface of the primary support by glue bonding; the toe orthotic device adjusts its angle by the rotary support, which facilitates the bandage to tighten the toes that need orthotics.

However, the toe deformity degree of each person is different, and the prior toe orthotic device can not fit the toe deformity degree of everyone; if the toe orthotic device does not match the human toe, it will affect the achievement of the toe orthotic device and causes discomfort in use.

SUMMARY OF THE INVENTION

The utility model aims to provide an adjustable toe orthotic device with simple structure and fine adaption to different toes.

The purpose of the utility model is achieved as follows:
an adjustable toe orthotic device, comprising:
a primary support and a secondary support connected by rotation; the primary support and secondary support are both provided with bandages, separately used for tying the primary support to the foot arch and the secondary support to the toe;
the pivots of the primary support and secondary support are provided with a lifting component, the lifting component is used to abut on the deformity point of the toe, and the lifting distance of the lifting component is adjusted to adapt to different degrees of toe deformity.

Furthermore, the lifting components comprise a lifting rod; the pivots of the primary support and secondary support are provided with openings, in which the lifting rods are arranged.

Furthermore, the device also comprises a driving member; the lifting rod is provided with a groove, and both the surface of the driving member and the groove are provided with threads; the driving member is rotatably arranged in the lifting rod through the thread;

the lifting rod is provided with a convex portion, and the opening is provided with a sliding groove for placing the convex portion;

the driving member is axially limited at the pivot, and the lifting rod is moved axially in the opening by rotating the driving member.

Furthermore, the primary support/secondary support includes connected upper panel and lower panel, the upper panel and the lower panel are respectively provided with an upper opening and a lower opening on the pivot; the driving member is axially limited in the upper opening, and the lifting rod is arranged in the lower opening.

Furthermore, the driving member is also connected with a handle, and the driving member is driven by the handle.

Furthermore, the driving member and the handle respectively abut on the two sides of the upper panel at the pivot, and connect to each other through the upper opening.

Furthermore, the lifting component comprises an airbag provided on the pivot; the primary support or the secondary support is provided with an air pump component connected to the airbag and a power source for supplying power to the air pump component; when the airbag is inflated, the airbag lifts up and abuts on the deformity point of the toe.

Furthermore, the airbag is also connected with a deflation valve; when the deflation valve is opened, the airbag gradually retracts with the air releasing through the deflation valve.

Furthermore, the deflation valve is connected with a circuit board that drives the switching of the deflation valve; the retraction degree of the airbag is altered by controlling the conduction time of the deflation valve.

Furthermore, the primary support is also provided with a gasket, and the gasket covers the primary support and an abutting surface; the lifting rod is connected with the abutting surface; Velcro™ is arranged on the abutting surface to connect the gasket.

Compared with the prior art, the utility model has the following outstanding and beneficial technical effects:

1. The utility model abuts the deformity point of the use's toe by setting a lifting surface on the pivot of the toe orthotic device. Generally, the pivot of the toe orthotic device corresponds to the joint point of the use's toe, which is just the deformity point of the toe. Therefore, adjust the lifting degree of the abutting surface to adapt to different toe deformity degrees, so that the abutment of the toe orthotic device is always in the state that best fits the use's toe deformity.
2. By the threaded lifting mechanism, the utility model increases the abutting stability of the lifting rod first through the support of the upper and lower supporting surfaces; meanwhile, the threaded lifting adjustment has the advantage of precise adjustment distance, which contributes to adjusting to the most comfortable state.
3. The utility model is provided with a handle, which is convenient for the user to operate and adjust the mechanism.
4. The utility model adjusts the height in a form of air pump, thereby changing manual adjustment to automatic adjustment, which reduces the operation of users and makes it more convenient.

Figure 1:
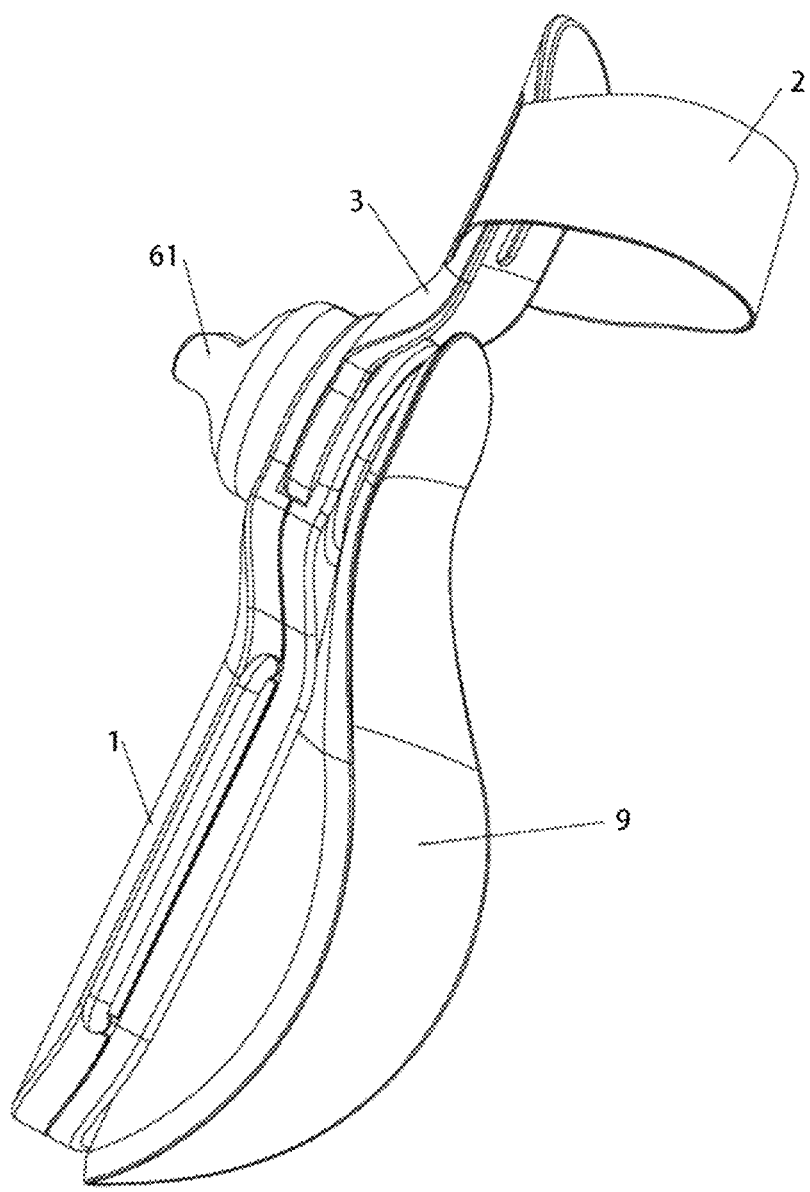
FIG. 1 is a schematic structure diagram of the embodiment 1.

Meaning of the reference numbers:

1 refers to the primary support; 11 refers to the upper panel; 112 refers to the upper opening; 12 refers to the lower panel; 122 refers to the lower opening; 123 refers to the sliding groove; 13 refers to the rotary rod; 2 refers to the bandage; 3 refers to the secondary support; 31 refers to the spring clip; 4 refers to the abutting surface; 5 refers to the lifting rod; 51 refers to the groove; 52 refers to the thread; 53 refers to the convex portion; 6 refers to the driving member; 61 refers to the handle; 8 refers to the airbag; 81 refers to the deflation valve; 82 refers to the air pump component; 9 refers to the gasket.

DETAILED DESCRIPTION OF THE PREFERRED EMBODIMENTS

The utility model is further described hereinafter with reference to the embodiments:

Embodiment 1

An adjustable toe orthotic device, comprising a primary support 1 and a secondary support 3 that are rotatably connected; both the primary support 1 and the secondary support 3 are provided with bandages 2, which are used to tie the primary support 1 to the foot arch and the secondary support 3 to the toe; the primary support 1 and the secondary support 3 are used to connect the use's foot to facilitate toe orthotics.

The utility model abuts on the deformity point of the use's toe by setting a lifting surface on the pivot of the toe orthotic device. Generally, the pivot of the toe orthotic device corresponds to the joint point of the use's toe, and the joint point is the deformity point of the toe. Therefore, the lifting degree of the abutting surface is adjusted to adapt to different toe deformity degrees, so that the abutment of the toe orthotic device is always in the state that best fits the use's toe deformity.

Furthermore, the lifting component comprises a lifting rod 5; an opening is provided on the pivot of the primary support 1 and the secondary support 3, and the lifting rod 5 is arranged in the opening.

The lifting rod 5 is provided with a groove 51, the surface of the driving member 6 and the groove 51 are both provided with thread 52, and the driving member 6 is rotatably arranged in the lifting rod 5 through thread 52;

the lifting rod 5 is provided with a convex portion 53 outside, and the opening is arranged with a sliding groove 123 for placing the convex portion 53;

the driving member 6 is axially limited at the pivot; rotate the driving member 6 to make the lifting rod 5 axially move in the opening.

Figure 2:
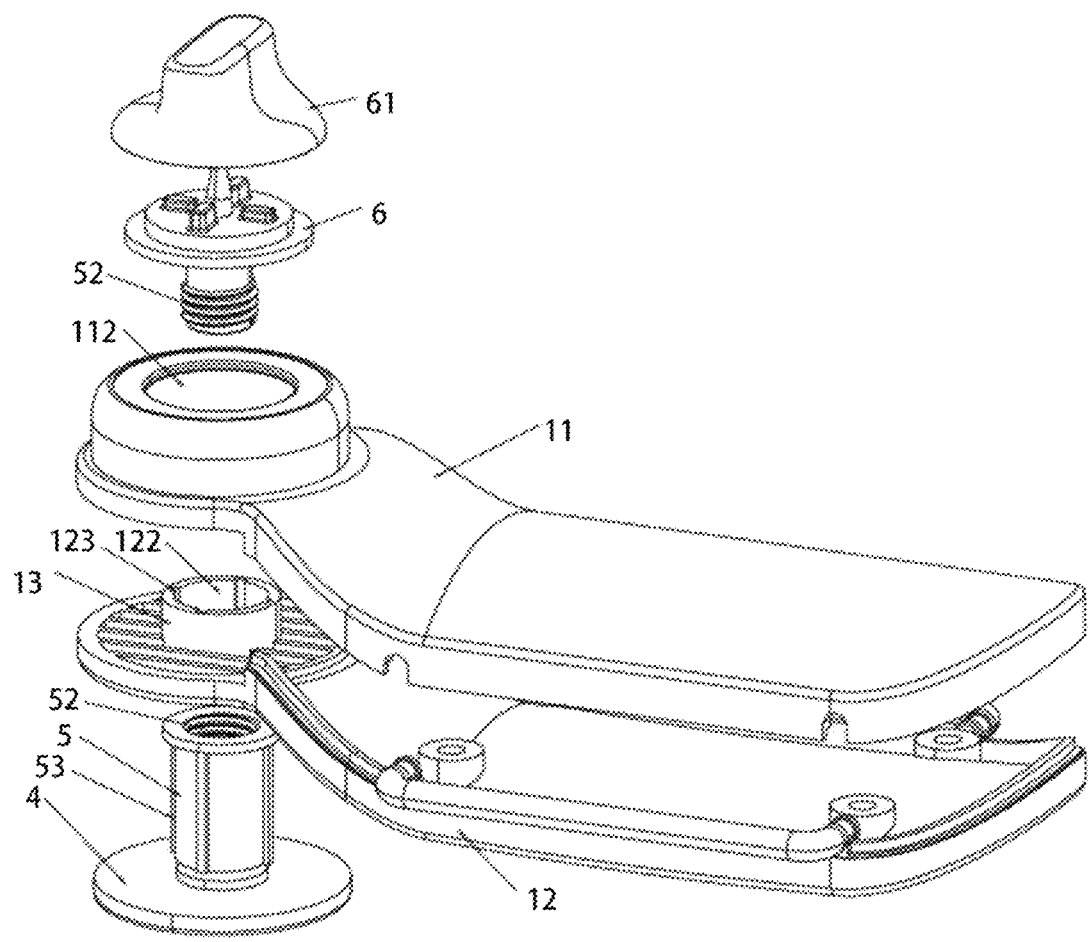
FIG. 2 is a exploded schematic view of the embodiment 1.
Figure 3:
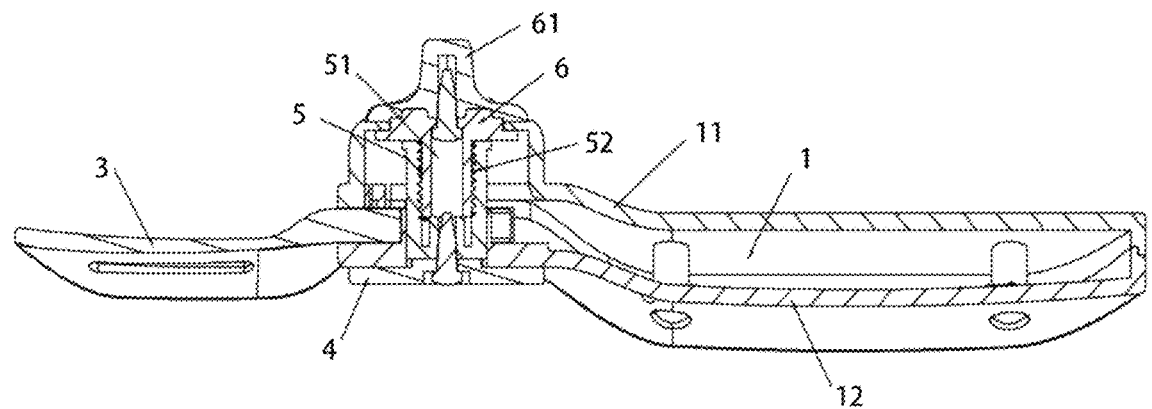
FIG. 3 is a side sectional view of the embodiment 1.

Specifically, as shown in FIG. 2 and FIG. 3, the primary support 1 includes an upper panel 11 and a lower panel 12 connected to each other; the upper panel 11 and the lower panel 12 are respectively provided with an upper opening 112 and a lower opening 122 at the pivot; there is a certain space between the upper panel 11 and the lower panel 12 for accommodating the above-mentioned lifting structure; the driving member 6 is axially limited in the upper opening 112, and the lifting rod 5 is arranged in the lower opening 122; in other embodiments, the above-mentioned lifting structure can also be installed in the primary support 3; that is, the secondary support 3 is composed of an upper panel 11 and a lower panel 12, the driving member 6 is axially limited in the upper opening 112 of the secondary support 3, and the lifting rod 5 is arranged in the lower opening 122 of the secondary support 3. In the operation, the user handles the driving member 6 to rotate; as shown in FIG. 2 and FIG. 3, the driving member 6 is provided with a handle 61; specifically, fixed connect the handle 61 to the driving member 6 by screws; the handle 61 is for the user to grasp; it is exposed outside the primary support 1, which is convenient for the user to grasp to drive the driving member 6 to rotate. When the driving member 6 rotates, it will drive the lifting rod 5 connected with the thread 52 of the driving member 6 to rotate at the same time; however, because the convex portion 53 on the lifting rod 5 limits the rotation, the lifting rod 5 will slowly move outwards due to the engagement of the lifting rod 5 with the thread 52 of the driving member 6, thereby driving itself to move.

Furthermore, the lifting rod 5 is also connected with an abutting surface 4, and the abutting surface 4 is lifted by moving the lifting rod 5; the abutting surface 4 can increase the contact area between the lifting component and the user, thereby the wearing is more comfortable. The primary support 1 is also provided with a gasket 9; the gasket 9 covers the primary support 1 and the abutting surface 4; for the convenience of installing the gasket 9 on the abutting surface 4, the abutting surface 4 is provided with Velcro™ to connect the gasket 9.

In addition to the above structure, the lifting component can also be a simple thread 52 adjustment structure, which is obtained by opening a threaded hole on the pivot. In this case, the lifting rod 5 is a screw rod arranged in the threaded hole, and is lifted along its threads by rotating the screw rod. A abutting surface 4 and a driving member 6 can be set at the two ends of the screw rods. The driving member 6 can be the rotary handle 61. Rotate the driving member 6 to drive the screw 52 lifting in the hole of the screw 52, thereby driving the abutment surface 4 connected with the rod of the screw 52 to lift. However, the structure of the threaded rod merely has vertical support, therefore its stability is weak, which tends to cause deviation, and damage in the long-term use. Moreover, the lifting motion of the screw is rotating lifting. Since the gasket 9 is fixed on the abutting surface 4 by Velcro™, if the screw is rotated and lifted, the gasket 9 must be removed for lifting adjustment, otherwise the operation cannot be performed.

Therefore, the advantages of adopting the structure shown in FIG. 2 and FIG. 3 are as follow. The adjustment structure can be adjusted without turning the lifting rod 5, and the screw adjustment structure is accurate, which is convenient for the user to adjust to the most comfortable distance; moreover, the support structure of the upper panel 11 and the lower panel 12 effectively increases the stability of the overall structure, which prevents the abutting surface 4 from deviating due to the instability of the lifting structure, so that the best abutting effect cannot be achieved.

Furthermore, the driving member 6 and the handle 61 abut on both sides of the upper supporting surface 111 respectively, and are connected through the upper opening 112; in this case, the driving part 6 and the handle 61 are respectively fixed on both sides of the upper supporting surface 111 for vertical limit; however, the driving member 6 is not fixed in the upper opening 112, so the driving member 6 can still be rotated by handle 61; therefore, through the above structure, while limiting the driving member 6, the driving member 6 can be rotated in the upper opening 112. In addition to the above-mentioned limit structure, another limit method can also be adopted. Specifically, provide a slot along the upper opening 112 and a boss on the driver 6, locate the boss in the slot, so that the driver 6 can be rotated while being vertically limited; however, the structure is more complicated to manufacture and not suitable for volume production.

It is also viable to not arrange the driving part 6 inside the upper opening 112. When the primary support 1 or the secondary support 3 is not composed of the upper panel 11 and the lower panel 12, arrange an additional support frame on the primary support 1 or the secondary support 3. An axial limit structure is provided on the support frame for installing the driving part 6.

Embodiment 2

Figure 4:
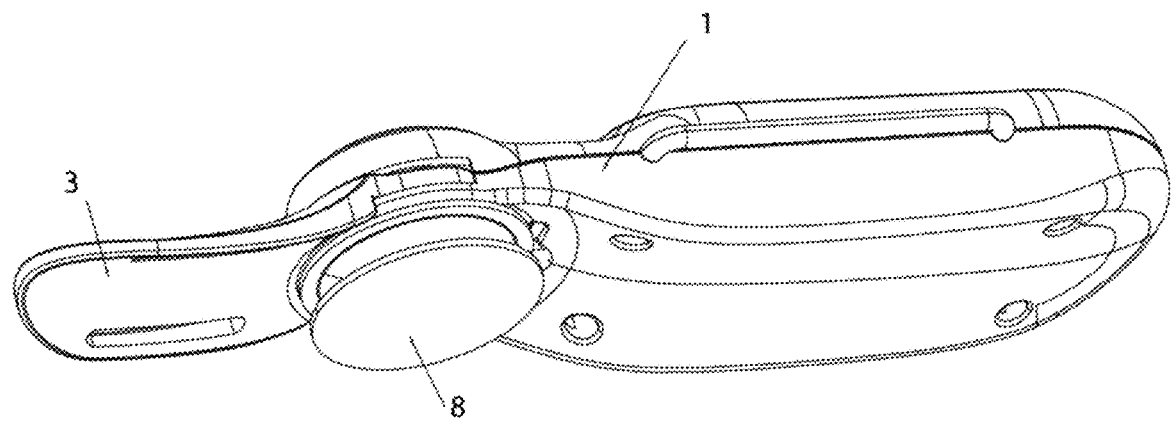
FIG. 4 is a schematic structure diagram of the embodiment 2.
Figure 5:
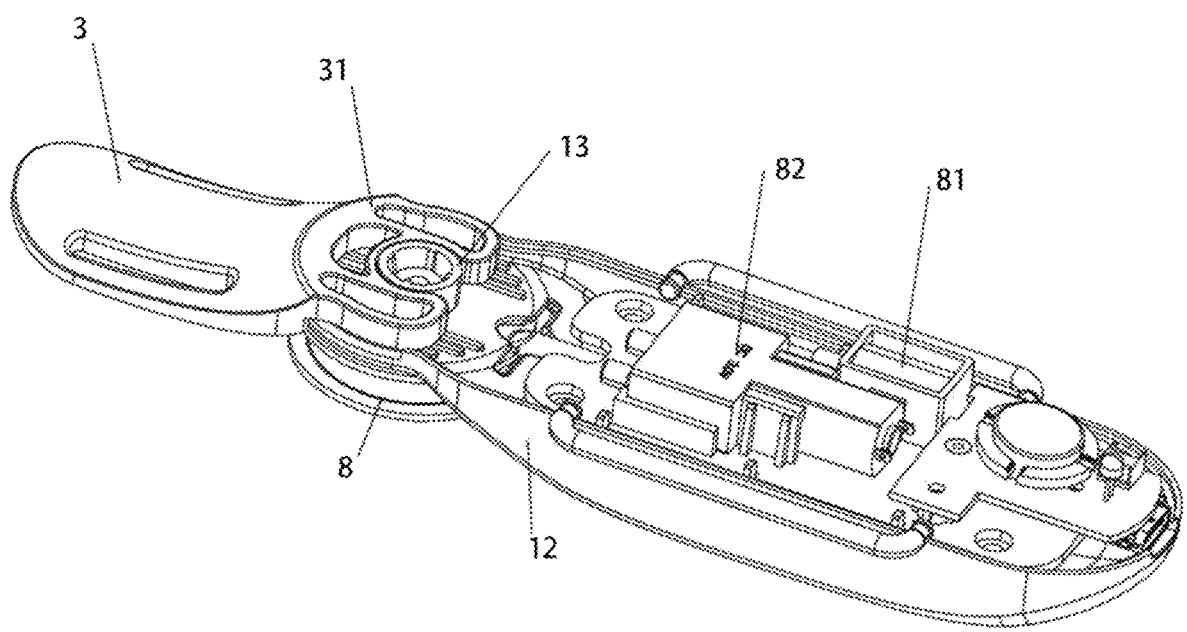
FIG. 5 is a schematic diagram of the air pump component of the embodiment 2.

As shown in FIG. 4 and FIG. 5, most structures in this embodiment are the same as those in the embodiment 1. The differences are that, the lifting component includes an airbag 8 arranged on the pivot; the primary support 1 or the secondary support 3 is provided with an air pump component 82 connected to the airbag 8 and a power source for supplying power to the air pump component 82. Inflate the airbag 8 by the air pump component 82, thereby the airbag 8 lifts up and abuts on the deformity point of the toes. Specifically, the airbag 8 is arranged under the lower panel 12, and the lower panel 12 on the side of the airbag 8 is provided with an opening connecting the inner cavity of the primary support 1; the opening is for placing the air tube, and the two ends of the air tube are respectively connected to the air bag 8 and the air pump component 82. The inner cavity of the primary support 1 is also provided with several control buttons for controlling the air pump component 82.

The advantage of adopting the air pump is that, compared with Embodiment 1, the manual adjustment changes to automatic adjustment, which is comparatively more convenient and reduces the operation steps, and saves worry and effort.

Furthermore, the airbag 8 also connects with a deflation valve 81. When the deflation valve is opened, the gas in the airbag 8 is released through the deflation valve 81 and the airbag gradually retracts. As shown in FIG. 4, the deflation valve 81 is arranged on one side of the air pump component 82, and is connected with a circuit board that drives the switching of the deflation valve 81. When using the toe orthotic device, if the airbag 8 always abuts on the deformity point of the use's toe, the long-term contact will cause uncomfortable feelings. Therefore, the effect of adding the deflation valve 81 is that by gradually retracting the airbag 8 through the slow deflation of the deflation valve 81, it correspondingly alleviates the discomfort caused by the orthotics, and meanwhile reminds the user of the use duration. The user can control the retraction degree of the airbag 8 by controlling the conduction time of the deflation valve 81, meaning the longer the conduction time is, the more it retracts; it is also feasible to adjust the retraction degree of the airbag 8 within a predetermined time by changing the size of the deflation valve 81.

Furthermore, the primary support 1 is provided with rotary rod 13, and the secondary support 3 is provided with spring clip 31; when the secondary support 3 is rotatably arranged on the primary support 1, the spring clip 31 is clamped on the rotary rod 13. As shown in FIG. 5, the spring clip 31 is specifically a plastic clip with several vias; the spring clip 31 includes a left claw and a right claw, both of which are provided with the vias, and the plastic clip has a certain elasticity through the vias; the ends of the left claw and the right claw are bent inwardly to facilitate the clamping on the rotary rod 13.

When using the spring clip 31, turn the spring clip 31 towards the rotary rod 13 and push forward, making the claws of the spring clip 31 overcome its own structure to expand outward; until the spring clip 31 is on the rotary rod 13, it is restored by its own elasticity; in this case, the spring clip 31 is clamped on the rotary rod 13, and the secondary support 3 can be rotated along the clamping point by the clamping structure of the spring clip 31. Preferably, the clamping mouth of the spring clip 31 is circular and the rotary rod 13 is also cylindrical, which facilitates the rotation of the secondary support 3. Therefore, through the above structure, the secondary support 3 can be easily removed from the primary support 1, which facilitates the replacement of the secondary support 3. When in use, it is feasible to adapt to the toes with different deformity degrees by replacing the secondary support 3 with different offset angles.

The embodiments are only preferred embodiments of the utility model, and do not limit the protection scope of the utility model accordingly. Therefore, all equivalent changes made in accordance with the structure, shape and principle of the utility model shall be covered by the protection scope of the utility model.

The invention claimed is:

1. An adjustable toe orthotic device, comprising:
   a primary support and a secondary support connected by rotation; the primary support and secondary support are both provided with a pivot and a bandage, separately used for tying the primary support to an arch of a foot and the secondary support to a foot's toe;
   both pivots of the primary support and secondary support are provided with a lifting component, the lifting component is used to abut on a deformity point of the foot's toe, and a lifting distance of the lifting component is adjusted to adapt to different degrees of foot's toe deformity;
   the lifting component comprises a lifting rod; both pivots of the primary support and secondary support are provided with openings, in which the lifting rod is arranged;
   also comprises a driving member; the lifting rod is provided with a groove, and both surface of the driving member and the groove are provided with threads; the driving member is rotatably arranged in the lifting rod through the threads;
   the lifting rod is provided with a convex portion, and an opening is provided with a sliding groove for placing the convex portion;
   the driving member is axially limited at the pivot, and the lifting rod is moved axially in the opening by rotating the driving member.

2. The adjustable toe orthotic device according to claim 1, wherein the primary support/secondary support includes connected upper panel and lower panel, the upper panel and the lower panel are respectively provided with an upper opening and a lower opening on a pivot; the driving member is axially limited in the upper opening, and the lifting rod is arranged in the lower opening.

3. The adjustable toe orthotic device according to claim 2, wherein the driving member is also connected with a handle, and the driving member is driven by the handle.

4. The adjustable toe orthotic device according to claim 3, wherein the driving member and the handle respectively abut on the two sides of the upper panel at a pivot, and connect to each other through the upper opening.

5. The adjustable toe orthotic device according to claim 1, wherein the primary support is also provided with a gasket, and the gasket covers the primary support and an abutting surface; the lifting rod is connected with the abutting surface; Velcro™ fastener is provided on the abutting surface to connect the gasket.

* * * * *